United States Patent
Jak et al.

(10) Patent No.: US 10,551,308 B2
(45) Date of Patent: Feb. 4, 2020

(54) FOCUS CONTROL ARRANGEMENT AND METHOD

(71) Applicant: ASML Netherlands B.V., Veldhoven (NL)

(72) Inventors: Martin Jacobus Johan Jak, 's-Hertogenbosch (NL); Armand Eugene Albert Koolen, Nuth (NL); Gerbrand Van Der Zouw, Waalre (NL); Dirk Karel Margaretha Broddin, Terneuzen (NL)

(73) Assignee: ASML Netherlands B.V., Veldhoven (NL)

( * ) Notice: Subject to any disclaimer, the term of this patent is extended or adjusted under 35 U.S.C. 154(b) by 90 days.

(21) Appl. No.: 15/378,962

(22) Filed: Dec. 14, 2016

(65) Prior Publication Data

US 2017/0176328 A1 Jun. 22, 2017

(30) Foreign Application Priority Data

Dec. 22, 2015 (EP) .................................... 15202073
May 24, 2016 (EP) .................................... 16171065

(51) Int. Cl.
*G01N 21/00* (2006.01)
*G01N 21/956* (2006.01)
(Continued)

(52) U.S. Cl.
CPC ....... *G01N 21/474* (2013.01); *G01N 21/9501* (2013.01); *G01N 21/956* (2013.01);
(Continued)

(58) Field of Classification Search
CPC ......... G01N 21/474; G01N 2015/1452; G01N 15/1463; G01B 11/026; G06K 9/00127
See application file for complete search history.

(56) References Cited

U.S. PATENT DOCUMENTS 6,538,249 B1 * 3/2003 Takane ...................... G06T 5/50
 850/10
7,321,108 B2 1/2008 Watkins et al.
(Continued)

FOREIGN PATENT DOCUMENTS

WO WO 2012/083206 A1 6/2012
WO WO 2012/126718 A1 9/2012
(Continued)

OTHER PUBLICATIONS

Danzl et al., "Focus Variation—A Robust Technology for High Resolution Optical 3D Surface Metrology," Journal of Mechanical Engineering, vol. 57, No. 3, 2011; pp. 245-256.
(Continued)

*Primary Examiner* — Rebecca C Bryant
(74) *Attorney, Agent, or Firm* — Sterne, Kessler, Goldstein & Fox P.L.L.C.

(57) ABSTRACT

An inspection apparatus includes an optical system, which has a radiation beam delivery system for delivering radiation to a target, and a radiation beam collection system for collecting radiation after scattering from the target. Both the delivery system and the collection system comprise optical components that control the characteristics of the radiation and the collected radiation. By controlling the characteristics of one or both of the radiation and collected radiation, the depth of focus of the optical system may be increased.

20 Claims, 8 Drawing Sheets

(51) Int. Cl.
*G01N 21/47* (2006.01)
*G01N 21/95* (2006.01)
*G03F 7/20* (2006.01)

(52) U.S. Cl.
CPC ...... *G03F 7/70625* (2013.01); *G03F 7/70641* (2013.01); *G01N 2021/4704* (2013.01); *G01N 2021/4778* (2013.01); *G01N 2021/4792* (2013.01)

(56) References Cited

U.S. PATENT DOCUMENTS

| | | | |
|---|---|---|---|
| 8,711,346 | B2 | 4/2014 | Stokowski |
| 9,404,737 | B2 * | 8/2016 | Segale ............... G01N 21/6458 |
| 2002/0085271 | A1 | 7/2002 | Shafer et al. |
| 2003/0211411 | A1 | 11/2003 | Yung et al. |
| 2006/0033921 | A1 | 2/2006 | Den Boef et al. |
| 2006/0066855 | A1 | 3/2006 | Boef et al. |
| 2008/0073524 | A1 * | 3/2008 | Nishiyama ........... G01N 23/225 250/307 |
| 2008/0151228 | A1 | 6/2008 | Hugers |
| 2010/0116977 | A1 * | 5/2010 | Young ................... G01N 1/286 250/252.1 |
| 2010/0201963 | A1 | 8/2010 | Cramer et al. |
| 2010/0328655 | A1 | 12/2010 | Den Boef |
| 2011/0027704 | A1 | 2/2011 | Cramer et al. |
| 2011/0043791 | A1 | 2/2011 | Smilde et al. |
| 2011/0069292 | A1 | 3/2011 | Den Boef |
| 2012/0044470 | A1 | 2/2012 | Smilde et al. |
| 2012/0123581 | A1 | 5/2012 | Smilde et al. |
| 2013/0258310 | A1 | 10/2013 | Smilde et al. |
| 2013/0271740 | A1 | 10/2013 | Quintanilha |
| 2014/0002829 | A1 | 1/2014 | Kim et al. |
| 2014/0139814 | A1 | 5/2014 | Cramer et al. |
| 2014/0300890 | A1 | 10/2014 | Lange et al. |
| 2016/0109375 | A1 | 4/2016 | Pandev et al. |

FOREIGN PATENT DOCUMENTS

| | | |
|---|---|---|
| WO | WO 2013/178422 A1 | 12/2013 |
| WO | WO 2014/082938 A1 | 6/2014 |
| WO | WO 2016/050453 A1 | 4/2016 |

OTHER PUBLICATIONS

International Search Report and Written Opinion of the International Searching Authority directed to related International Patent Application No. PCT/EP2016/078758, dated Feb. 22, 2017; 12 pages.

* cited by examiner

FOCUS CONTROL ARRANGEMENT AND METHOD

FIELD

The present invention relates to a method and an arrangement for increasing depth of focus of an optical system in an inspection apparatus. In particular, the present invention relates to a method for controlling the radiation used in an optical system of an inspection apparatus so as to increase the depth of focus of the optical system.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 20120126718. Methods and scatterometers are also disclosed in US20110027704A1, US2006033921A1 and US2010201963A1. The targets used by such scatterometers are relatively large, e.g., 40 μm by 40 μm, gratings and the measurement beam generates an illumination spot that is smaller than the grating (i.e., the grating is underfilled). In addition to scatterometry to determine parameters of a structure made in one patterning step, the methods and apparatus can be applied to perform diffraction-based overlay measurements.

Diffraction-based overlay metrology using dark-field image detection of the diffraction orders enables overlay measurements on smaller targets. These targets can be smaller than the illumination spot and may be surrounded by product structures on a wafer. Multiple targets can be measured in one image. Examples of dark-field imaging metrology can be found in international patent applications US2010328655 A1 and US2011069292 A1 which documents are hereby incorporated by reference in their entirety. Further developments of the technique have been described in published patent publications US20110027704A, US20110043791A, US20120044470A US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938 A1 and US2014/0139814A1, respectively. The contents of all the mentioned applications are also incorporated herein by reference. The invention is not limited in application to any particular type of inspection apparatus, or even to inspection apparatuses generally.

One way of improving the performance of an inspection apparatus, is to increase the numerical aperture of the optical system. Increasing the numerical aperture of a system also decreases the depth of focus of the optical system. It is therefore necessary to increase the precision of focus control of the optical system, which in turn increases the risk of incorrectly focusing the optical system.

Furthermore, integrated circuits consist of increasing numbers of layers. Each layer increases the height of the structure of the integrated circuit. Additionally, certain types of circuits, such as 3D NAND memory structures or DRAM memory structures, may be oriented vertically rather than horizontally. Accordingly, the height variation of such structures may be significantly more than the depth of focus of existing metrology systems. As metrology targets typically consist of two target structures that are positioned in different layers of a particular product structure, the distance between two target structures of a metrology target typically increases proportionally with any increase in overall height of the integrated circuit structure.

In order to perform accurate metrology measurements, it is necessary to ensure that the metrology targets are correctly in focus of the optical system. The reduction in depth of focus, in combination with the increasing distance between the target structures, may result in only one of the two target structures being in focus at a particular time. This decreases the accuracy of the metrology measurements significantly.

SUMMARY

The inventors have recognized that it is possible to increase the depth of focus of an optical system in an inspection apparatus by controlling a characteristic of the radiation used in the optical system. This, for example, enables both target structures of a metrology target to be kept in focus at the same time. This, in turn, increases the accuracy of the metrology measurements carried out using the inspection apparatus.

In a first aspect, the invention provides a method for increasing depth of focus of an optical system in an inspection apparatus, comprising:

delivering radiation to a target by using a radiation beam delivery system;

collecting scattered radiation that has been scattered by the target using a radiation collection system;

receiving the collected scattered radiation using a radiation collection system; and controlling a controllable characteristic of at least one of the radiation or the collected scattered radiation to control a focus point of the optical system relative to the target, wherein the step of receiving comprises receiving collected scattered radiation representing a plurality of values of the controllable characteristic.

The invention further provides an inspection apparatus, comprising:

a radiation beam delivery system operable to deliver radiation to a target;

a radiation collection system operable to collect scattered radiation that has been scattered by the target;

a radiation collection system operable to receive the collected scattered radiation; and a radiation control system operable to control a controllable characteristic of at least one of the radiation or the collected scattered radiation to control a focus point of the optical system relative to the target, wherein the collected scattered radiation represents a plurality of values of the controllable characteristic.

The invention yet further provides a lithographic apparatus comprising an inspection apparatus as set forth above.

The invention yet further provides a computer program product containing one or more sequences of machine-readable instructions for implementing controlling steps in a method according to the invention as set forth above.

The invention yet further provides a computer program product containing one or more sequences of machine-readable instructions for implementing a processing step in a method according to the invention as set forth above.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
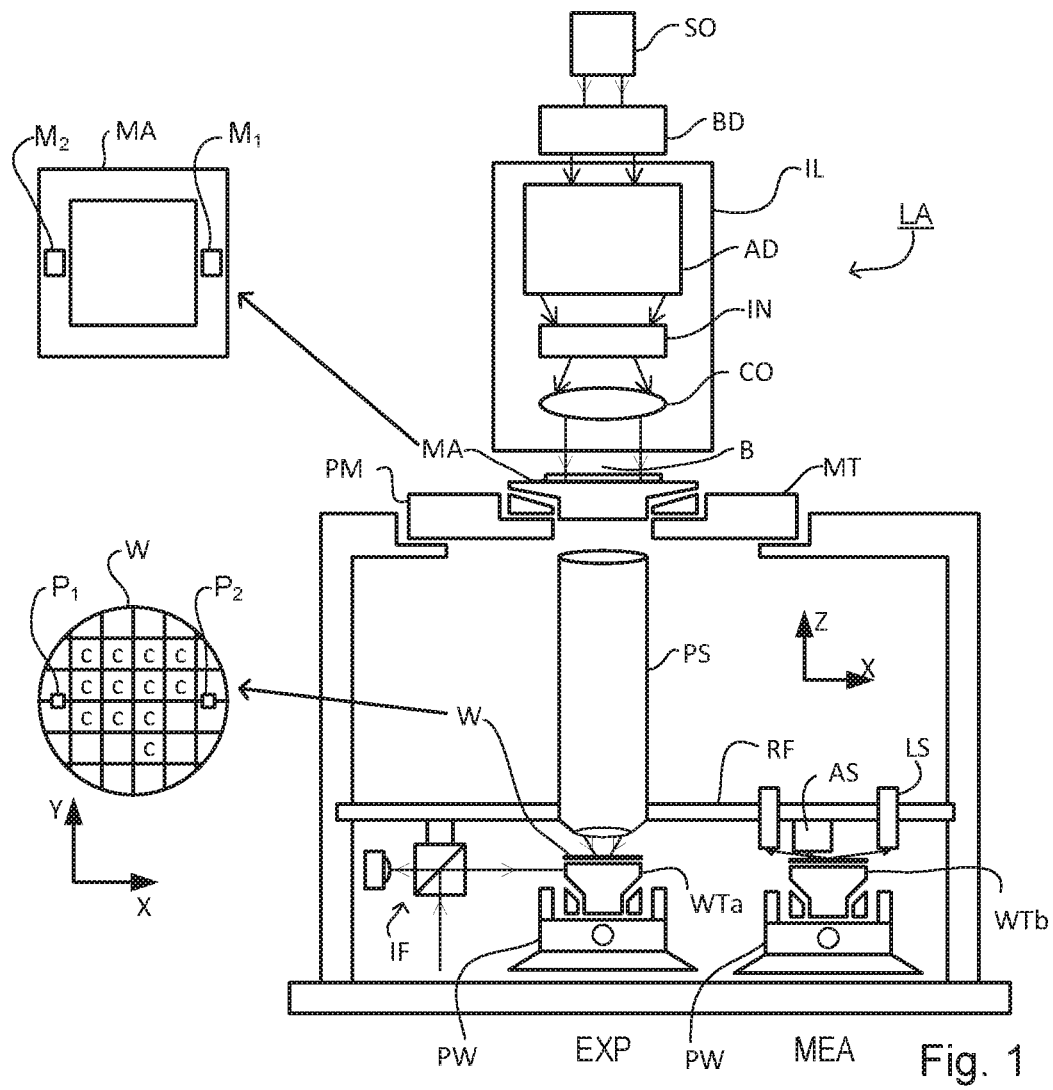
FIG. 1 depicts a lithographic apparatus.

FIG. 1 schematically depicts a lithographic apparatus. The apparatus comprises:

an illumination system (illuminator) IL configured to condition a radiation beam B (e.g. UV radiation or DUV radiation).

a support structure (e.g. a mask table) MT constructed to support a patterning device (e.g. a mask) MA and connected to a first positioner PM configured to accurately position the patterning device in accordance with certain parameters;

a substrate table (e.g. a wafer table) WT constructed to hold a substrate (e.g. a resist coated wafer) W and connected to a second positioner PW configured to accurately position the substrate in accordance with certain parameters; and a projection system (e.g. a refractive projection lens system) PL configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device".

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g. an interferometric device, linear encoder, 2-D encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the mask MA with respect to the path of the radiation beam B, e.g. after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e. a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
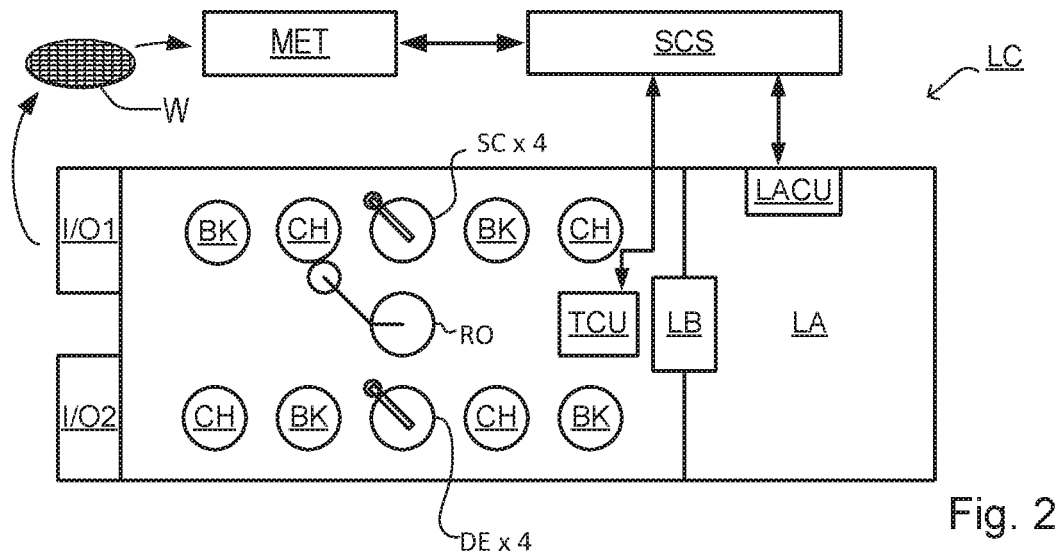
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
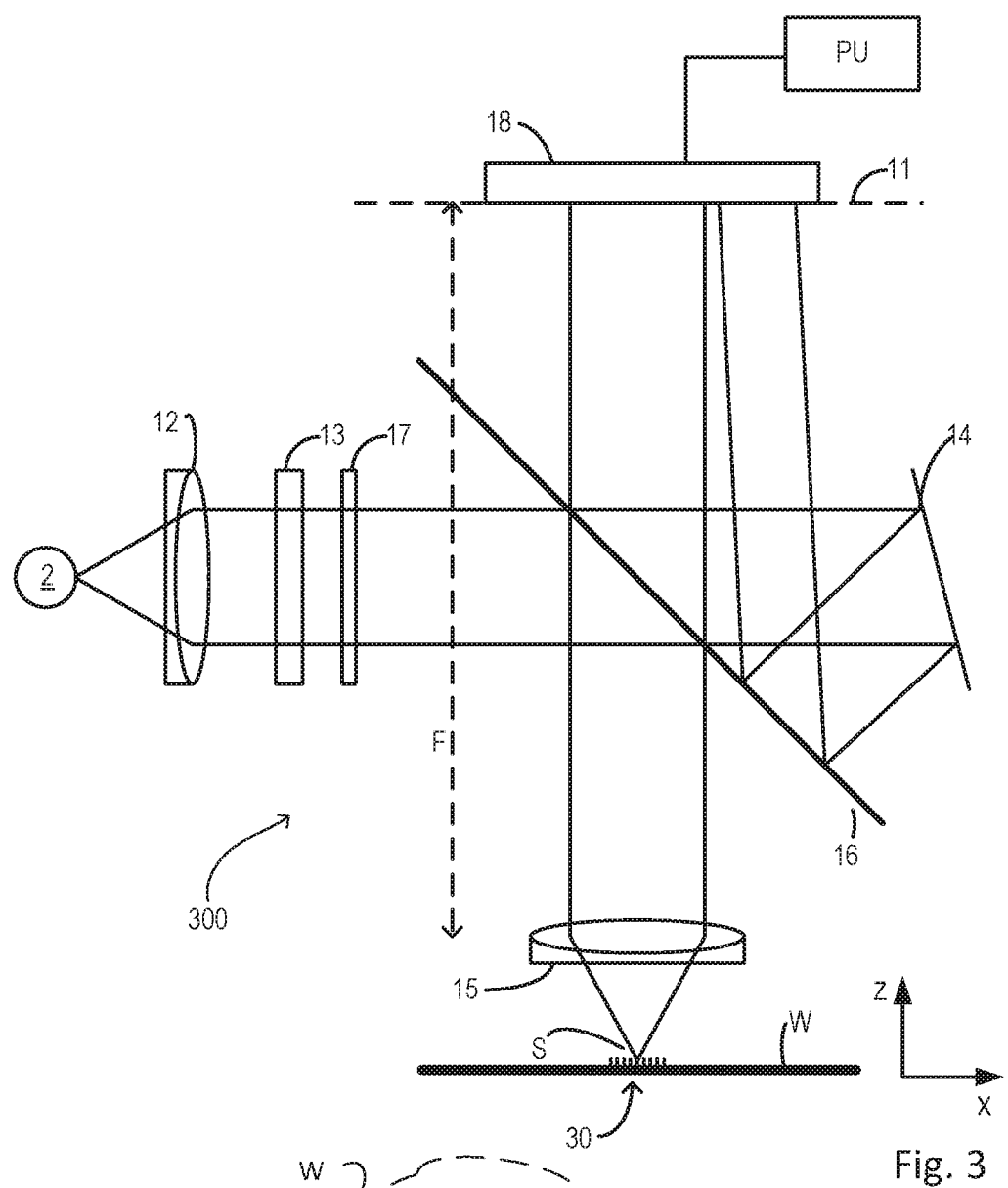
FIG. 3 depicts a known inspection apparatus arranged to perform angle-resolved scatterometry, as an example of an optical system in which a focus monitoring arrangement according to the present invention may be applied.

FIG. 3 depicts a known scatterometer 300. In this device, the radiation emitted by radiation source 2 is collimated using lens system 12 and transmitted through interference filter 13 and polarizer 17, reflected by partially reflecting surface 16 and is focused into a spot S on substrate W via a microscope objective lens 15, which has a high numerical aperture (NA), preferably at least 0.9 and more preferably at least 0.95. Immersion scatterometers may even have lenses with numerical apertures over 1.

As in the lithographic apparatus LA, one or more substrate tables may be provided to hold the substrate W during measurement operations. The substrate tables may be similar or identical in form to the substrate tables WTa, WTb of FIG. 1. In an example where the inspection apparatus is integrated with the lithographic apparatus, they may even be the same substrate tables. Coarse and fine positioners may be provided to a second positioner PW configured to accurately position the substrate in relation to a measurement optical system. Various sensors and actuators are provided for example to acquire the position of a target of interest, and to bring it into position under the objective lens 15. Typically many measurements will be made on targets at different locations across substrate W. The substrate support can be moved in X and Y directions to acquire different targets, and in the Z direction to obtain a desired focusing of the optical system on the target. An exemplary focusing system will be discussed in more detail in the following. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle which one of those is moving in the real world, or if both are moving.

The reflected radiation then passes through partially reflecting surface 16 into a detector 18 in order to have the scatter spectrum detected. The detector may be located in the back-projected pupil plane 11, which is at the focal length of the objective lens 15, however the pupil plane may instead be re-imaged with auxiliary optics (not shown) onto the detector. The pupil plane is the plane in which the radial position of radiation defines the angle of incidence and the angular position defines azimuth angle of the radiation. The detector is preferably a two-dimensional detector so that a two-dimensional angular scatter spectrum of a substrate target 30 can be measured. The detector 18 may be, for example, an array of CCD or CMOS sensors, and may use an integration time of, for example, 40 milliseconds per frame.

A reference beam is often used for example to measure the intensity of the incident radiation. To do this, when the radiation beam is incident on the beam splitter 16 part of it is transmitted through the beam splitter as a reference beam towards a reference mirror 14. The reference beam is then projected onto a different part of the same detector 18 or alternatively on to a different detector (not shown).

A set of interference filters 13 is available to select a wavelength of interest in the range of, say, 405-790 nm or even lower, such as 200-300 nm. The interference filter may be tunable rather than comprising a set of different filters. A grating could be used instead of interference filters. An aperture stop or spatial light modulator (not shown) may be provided in the illumination path to control the range of angle of incidence of radiation on the target.

The detector 18 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

The target 30 on substrate W may be a 1-D grating, which is printed such that after development, the bars are formed of solid resist lines. The target 30 may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS, and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processor PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the target 30 comprises one set of periodic features superimposed on another. The concepts of asymmetry measurement using the instrument of for instance FIG. 3 are described for example in published patent application US2006066855A1. Simply stated, while the positions of the diffraction orders in the diffraction spectrum of the target are determined only by the periodicity of the target, asymmetry in the diffraction spectrum is indicative of asymmetry in the individual features which make up the target. In the instrument of FIG. 3, where detector 18 may be an image sensor, such asymmetry in the diffraction orders appears directly as asymmetry in the pupil image recorded by detector 18. This asymmetry can be measured by digital image processing in unit PU, and calibrated against known values of overlay.

Figure 4:
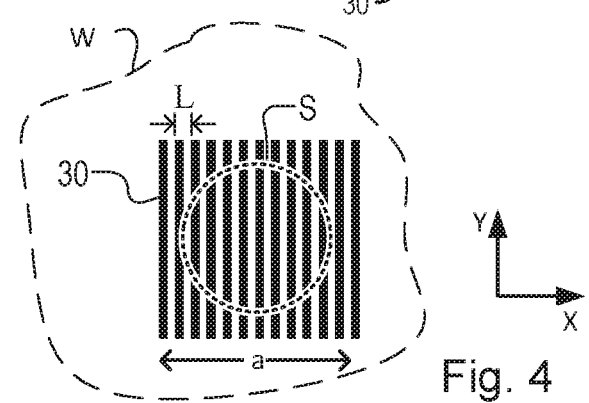
FIG. 4 illustrates the relationship between an illumination spot and a target grating in an example of the known scatterometers.

FIG. 4 illustrates a plan view of a typical target 30, and the extent of illumination spot S in the scatterometer of FIG. 3. To obtain a diffraction spectrum that is free of interference from surrounding structures, the target 30 in the known method is a grating larger than the diameter of the illumination spot S. The diameter of spot S may be over 10 or 20 µm and the grating width and length may be 30 or 40 µm square. The grating in other words is 'underfilled' by the illumination, and the diffraction signal is free from interference by product features and the like outside the target grating itself. The illumination arrangement 2, 12, 13, 17 may be configured to provide illumination of a uniform intensity across a pupil plane of objective 15. Alternatively, but including an aperture in the illumination path, illumination may be restricted to on axis or off axis directions. As described in prior applications cited above, a modified scatterometer can use so-called dark field imaging to capture diffracted radiation from several smaller targets, all falling within the same illumination spot S.

Figure 5:
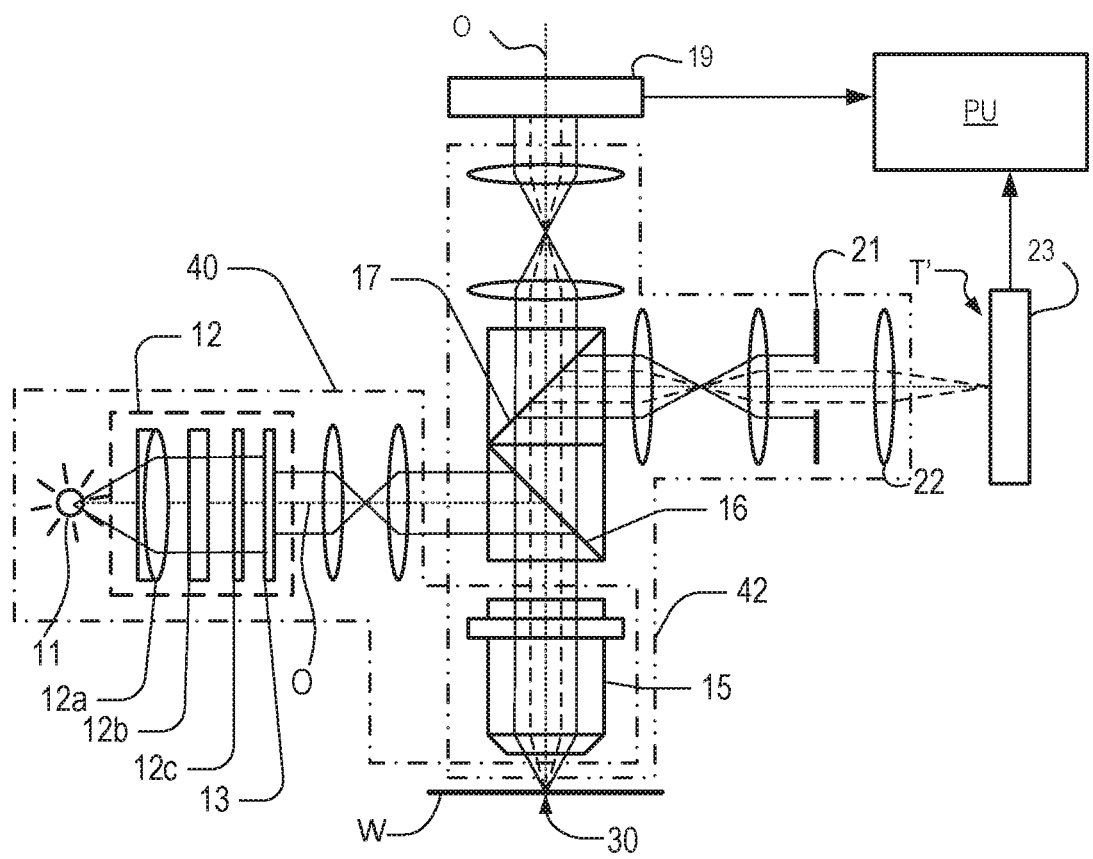
FIG. 5 illustrates schematically an inspection apparatus adapted to perform a known dark-field imaging inspection methods.

FIG. 5 shows in more detail an inspection apparatus implementing angle-resolved scatterometry by the same principles as the apparatus of FIG. 3, with additional adaptations for performing so-called dark field imaging. The apparatus may be a stand-alone device or incorporated in either the lithographic apparatus LA, e.g. at the measurement station, or the lithographic cell LC. An optical axis, which has several branches throughout the apparatus, is represented by a dotted line O.

The same reference numbers are used for components described already in the FIG. 3 apparatus. In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The aperture device may comprise a number of different specific apertures for use in dark imaging (or other types of imaging). It will be realized that the illumination system may comprise additional or alternative components as dictated by the requirements for the optical system. In one example, the illumination system comprises one or more optical components for tuning the focus of the illumination system. The radiation source 11, illumination system 12, first beam splitter 16 and objective lens 15 may collectively be referred to as a radiation beam delivery system 40.

Compared with the apparatus of FIG. 3, a second beam splitter 17 divides the collection path into two branches. In a first measurement branch, detector 19 records a scatter spectrum or diffraction spectrum of the target exactly as described above. This detector 19 may be referred to as the pupil image detector.

In the second measurement branch, imaging optical system 22 forms an image of the target 30 on the substrate W on sensor 23 (e.g. a CCD or CMOS sensor). An aperture stop 21 is provided in a plane that is in the collection path in a plane conjugate to the pupil-plane (it may also be called a pupil stop). Aperture stop 21 can take different forms, just as the illumination aperture 13 can take different forms. Typically, aperture stop 21 functions to block the zeroth order diffracted beam so that the image of the target formed on sensor 23 is formed only from the first order beam(s). This is the so-called dark field image, equivalent to dark field microscopy. The images captured by sensors 19 and 23 are output to image processor and controller PU, the function of which will depend on the particular type of measurements being performed. The first and second measurement branches, as well as the first and second beam splitters and the objective lens may collectively be referred to as a radiation collection system 42.

Regardless of the type of inspection apparatus, or other optical system, it is generally required to provide an automatic system for monitoring and adjusting focus of an optical system, such as the system that forms the scatterometers in FIGS. 3 and 5. If the spot S is not focused, then the illumination will fall on features other than the target (e.g. target 30 in FIG. 4), and the collected radiation will not allow an accurate measurement of the properties of the target. As mentioned already, focusing arrangements are known which pass a beam of radiation through the optical system and use some kind of detector system to obtain a signal representing focus error. For example, in published patent application US20080151228A, light reflected from the target is imaged onto two photodetectors with different focus offsets. Comparing the focused spot area between the two photodetectors allows an indication of defocus of the optical system to be obtained, and the direction of defocus to be identified. The US patent application illustrates various simple photodetectors that may be used to obtain a measure of spot area. Other types of focus arrangement can be envisaged, and the present disclosure is not limited to the technique of US20080151228A.

Figure 6:
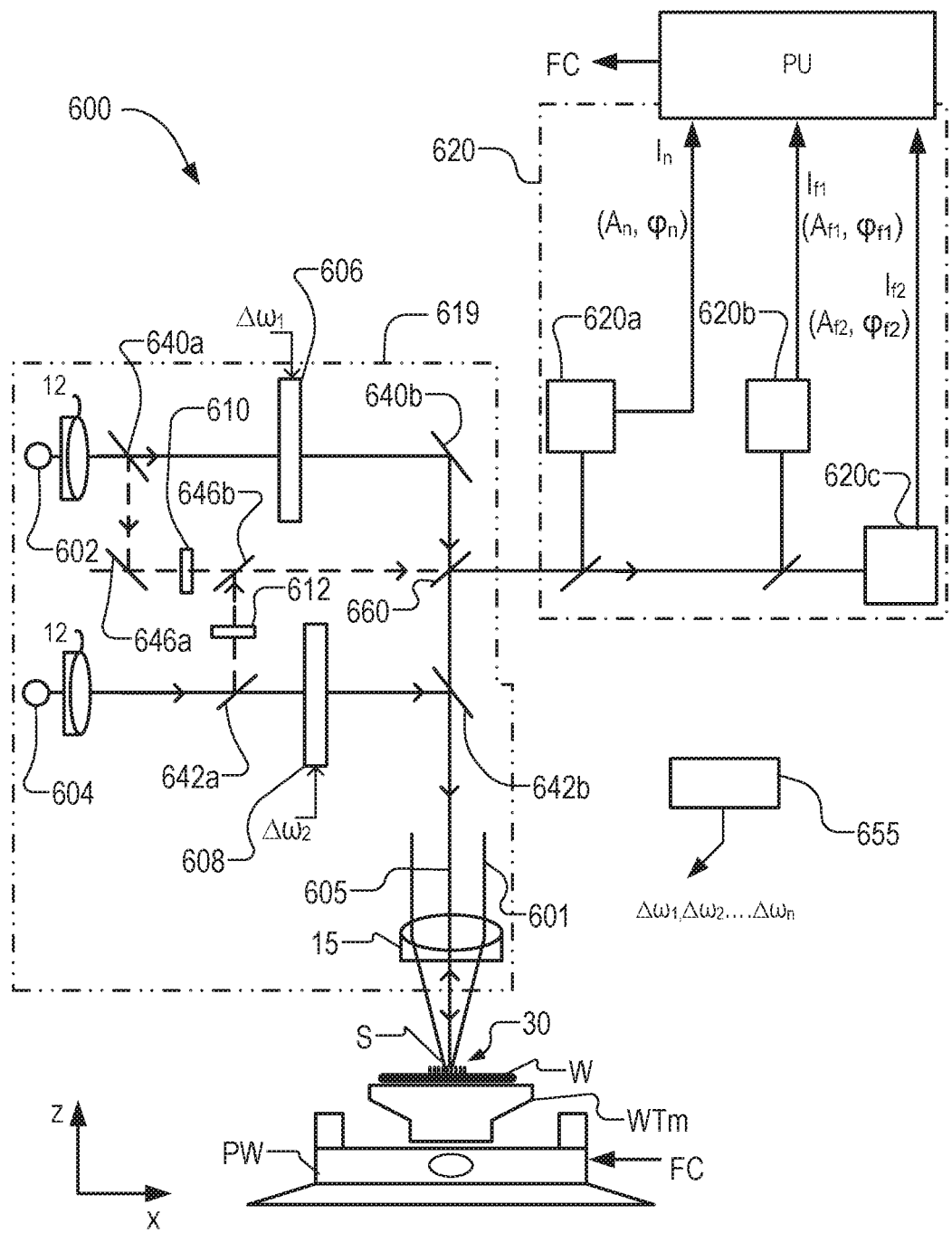
FIG. 6 is a schematic diagram of a focus monitoring arrangement in an inspection apparatus including lock-in detectors according to an embodiment of the invention.

FIG. 6 depicts in a simplified form a focus monitoring arrangement 600 implementing an heterodyne interferometric technique. FIG. 6 in particular provides a schematic view of optical paths for use in determining and controlling focus related properties of an inspection apparatus. With regard to the main function of the optical apparatus as a scatterometer or other inspection apparatus, a measurement illumination beam 601 follows an illumination path comprising optical components 12, 13, 16, 17 (not shown in this drawing) and objective lens 15 (shown). A collection path comprising the objective lens 15 for collecting radiation reflected by target 30 is also provided, as described above with reference to FIGS. 3 and 5. The radiation collected by optical components of the collection path is directed to a detector 18 connected to processor PU for target reconstruction or other purposes. The form and function of these may be the same as described above with reference to FIGS. 3 and 5, and thus will not be discussed in this section. Target 30 may be formed on a substrate W that has been patterned and processed using the lithographic apparatus of FIG. 1 and the cluster of processing tools described above with reference to FIG. 2. The optical system including objective lens 15 is mentioned for the sake of example only. It may be adapted for dark field imaging instead of or in addition to angle resolved scatterometry.

The focus monitoring arrangement and methods illustrated and described below can be applied in an optical system designed for a different kind of inspection (for example in a microscope), or for a purpose different from inspection (for example surface treatment, or optical recording). In particular, the arrangements of the present disclosure can also be applied to focusing of the projection system PS in the lithographic apparatus LA, or ancillary systems such as the alignment sensor AS. Indeed the optical system of the focus monitoring arrangement may or may not be part of (or share parts with) a functional optical system that is performing inspection or treatment of a target. The optical system of the focus monitoring arrangement may be ancillary to another functional system which is monitored and/or controlled indirectly using focusing of the optical system of the focus monitoring arrangement. In these cases, the optical system through which focusing is monitored is not the same as the functional system performing inspection and/or processing of the target. In the field of lithography, for example, the functional system may be an electron beam (e-beam) patterning apparatus, such as are used to make the reticle (patterning device) M. Other examples may be laser or mechanical machining or surface treatment apparatuses. Provided the focus monitoring arrangement is coupled to and calibrated with the functional system, a desired monitoring and/or control function may be implemented.

Focusing of the illumination spot S on target 30 is achieved by a suitable mechanism which may involve moving elements within the optical system, and/or moving the optical system and substrate bodily in relation to one another. For the sake of example in this illustration, substrate W is supported by a substrate table WTm similar to the substrate tables WTa and WTb of the lithographic apparatus. Positioners PW control the height of the substrate in response to a focus control signal FC generated by processor PU. Positioners PW control the position of substrate W in X and Y directions also, to bring each target of interest into position beneath the objective lens 15.

Focus monitoring arrangement 600 in this example comprises a focusing beam delivery system 619, which comprises a first radiation source 602 and a second radiation source 604, each with an associated lens system. Focusing radiation 605 passes through objective lens 15 to be reflected from target 30. The arrangement further includes a first frequency shifter 606, a second frequency shifter 608, a first attenuating device 610, a second attenuating device 612 and a focus detection system 620 including a normalization signal detector 620a and first and second lock-in detectors 620b and 620c. These components are arranged in an optical system which defines effectively several optical paths. Generally speaking, as in a known apparatus, there is a focusing beam delivery system for delivering focusing radiation 605 to the target and a focusing beam collection system for collecting reflected radiation and delivering it to detection system 620. More specifically, arrangement 600 comprises a first illumination path, delivering a first focusing radiation to the objective lens and the target. The first illumination path includes radiation source 602, first frequency shifter 606 and optical components 640a (e.g. beam splitter) and 640b (e.g. mirror). Further, the arrangement 600 includes a second illumination path, delivering second focusing radiation to objective lens and the target. The second illumination path includes second radiation source 604, second frequency shifter 608 and optical components 642a (e.g. a beam splitter) and 642b (e.g. a mirror). As explained further below the first and second focusing radiation differ in their color (wavelength range). First focusing radiation has a first wavelength range and second focusing radiation has a second wavelength range.

Additionally, there is provided a heterodyne reference system, exploiting the frequency shifts introduced by frequency shifters 606, 608, as explained below. The reference system includes a first reference path, delivering first reference radiation to the detection system 620, bypassing the objective lens and target. The first reference path includes first attenuating device 610 and optical component 646a (e.g. a mirror) as shown. Similarly a second reference path is provided for delivering second reference radiation to the detection system 620. The second reference path includes second attenuating device 612 and optical component 646b (e.g. a mirror). The collection system, defining a collection path for the focusing radiation 605 after it is reflected from target 30, comprises objective lens 15 and optical component 660 (e.g. a mirror). It will be noted that, in the present example, the objective lens and the optical component are comprised in both the focusing beam delivery system as well as the focusing beam collection system. However, it is, in principle, possible for the delivery and collection systems to comprise separate components. It will further be noted that the collection system may comprise additional components to those shown in FIG. 5.

A frequency source 655 provides first and second reference frequencies $\Delta\omega_1$ and $\Delta\omega_2$ to the first and second frequency shifters 606 and 608, respectively. A selected one of these reference frequencies is also provided to the first and second lock-in detectors 620b and 620c. These detectors may be single pixel photodiodes, or multi-pixels or multi-zone detectors, as described in the prior patent application mentioned above. Detection system 620 includes processor PU receives data from detectors 620a, 620b, 620c and uses these to generate focus control signal FC. It may be envisaged that a processor PU is implemented by software sharing the same processing hardware as processor PU shown in FIGS. 3 and 5 for the metrology functions. However, a dedicated sub-processor can be provided to implement the focus monitoring and control functions, if desired.

The mentioned beam paths can be implemented in many different layouts, and a particular configuration of mirrors 640b, 642b, 646a, 646b and 660 and beam splitters (BS) 640a, 642a is shown schematically here, only for illustration of the principles of the design. Not shown in the drawing are numerous components that would be included in a practical system, including for example lenses or other focusing elements. These can be adapted readily from the known apparatus and do not need to be described in detail. Additional beam paths for different functions (for different types of measurement) can also be provided.

As discussed above, one effect of increasing the numerical aperture (NA) is that the depth of focus of the optical system is decreased. Further, product structures comprise increasing number of layers, which increases the height of the product structures. In particular, certain product structures, such as 3D NAND memory structures or DRAM memory structures, may be taller than the depth of focus of the optical system. This also increases the vertical separation between the upper and lower target structures used to perform metrology. As a result, it is not possible for the optical system to keep both the upper and the lower gratings within acceptable focus at the same time. As discussed, this negatively impacts the accuracy of any measurements carried out.

Figure 7:
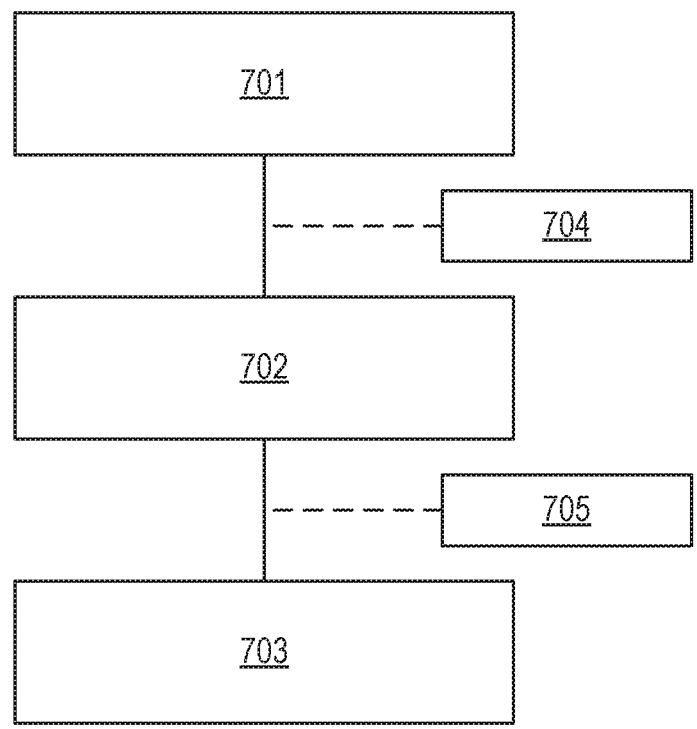
FIG. 7 illustrates a method according to an embodiment of the invention.

FIG. 7 illustrates an exemplary method for an optical system in an inspection apparatus (such as the one described with reference to FIG. 5). It is of course to be noted that the optical system described above is described purely for exemplary purposes, and that any suitable optical system could be used to carry out the method. In a first step 701, radiation is delivered to a target using a radiation beam delivery system (e.g. the radiation beam delivery system 40 of the inspection apparatus shown in FIG. 5).

In a second step 702, the radiation scattered by the target is collected by a radiation collection system, e.g. by radiation collection system 42 as described above with reference to FIG. 5.

In a third step 703, the collected radiation is received at a radiation collection system, such as a detector. In the present example, the collected radiation arrives at detector 23. The collected radiation may later be processed in a suitable fashion, e.g. by processing unit PU. The radiation collection system may in some examples comprise additional optical components to appropriately guide and/or control the collected radiation.

The method illustrated in FIG. 7 further comprises one or both of controlling steps 704 or 705, which will now be described in turn.

In a first controlling step 704, a characteristic of the radiation is controlled. Any suitable characteristic of the radiation may be controlled, for example the position of the focal point of the radiation. In one example, the characteristic to be controlled may be the position of a focal point of the radiation. In another example, the characteristic may comprise the beam waist of a coherent radiation beam (e.g. a laser beam). Other specific controllable characteristics may be envisaged by the skilled person.

The characteristic may be controlled in any suitable fashion and using any suitable components of the radiation beam delivery system. Taking one of the above examples, the characteristic is the position of a focal point of the radiation. In such an example, the controlling step may comprise controlling the position of the focal point of the radiation, such as (but not limited to): varying the focal length, or varying the position of one or more optical components of the optical system to change the position of the focal point without varying the focal length. In some examples, the position of the focal point along the direction of propagation of the radiation is controlled. In other examples, the position of the focal point may be controlled in three dimensions. Two specific, non-limiting, examples will be discussed in greater detail below.

Any suitable component, or combination of components, of the radiation beam delivery system 40 may be translated or otherwise moved in any suitable fashion. In the following, only the term "translate" is used for clarity, but it will be understood that the components can be both translated and rotated in any suitable direction. For example, some components may be translated, but not rotated. Other components may be rotated, but not translated. Yet other components may be both translated and rotated. In some examples, only a single component is translated. This minimizes the amount of force required to change the position of the focal point, which decreases the response time of the system. In one example, the objective lens 15 may be moved in the Z-direction in order to change the position of the focal point.

Similarly, in a second controlling step 705, a characteristic of the collected radiation is controlled. The second controlling step is substantially identical to the first controlling step, although the components of the radiation collection system 42 are actuated rather than those of the radiation beam delivery system. In other terms, any suitable component of the radiation collection system may be used to control the characteristic of the collected radiation.

The collected radiation may subsequently be processed in a suitable manner by a processing unit (e.g. processing unit PU of FIG. 5).

Two specific, non-limiting, examples of the controlling step will now be discussed with reference to FIGS. 8 and 9.

Figures 8A, 8B:
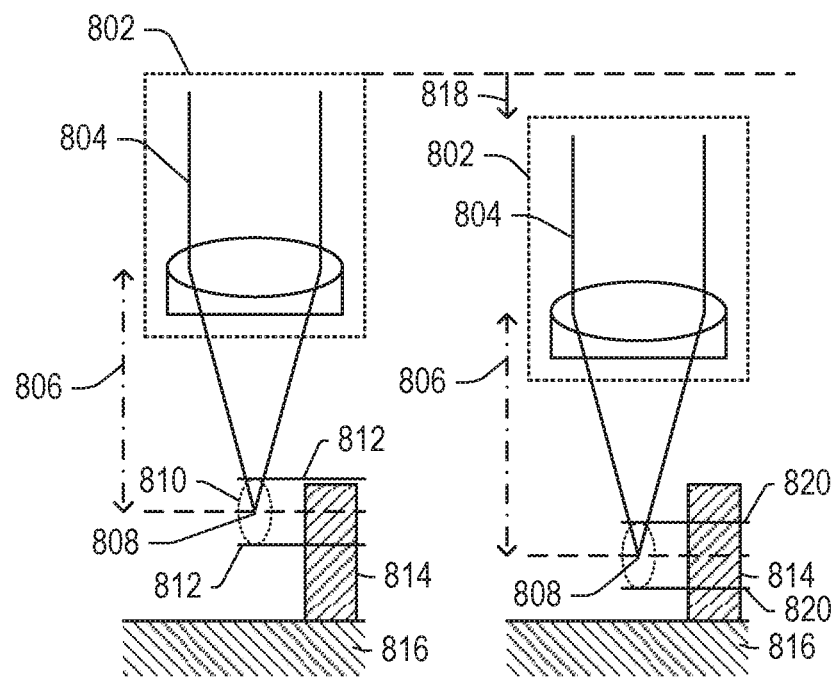
FIGS. 8A-8D show a first principle of implementing a controlling step of the method of FIG. 7.

FIG. 8 illustrates a first exemplary principle of a controlling step of the method disclosed in FIG. 7. In FIG. 8(a), a radiation beam delivery system 802 delivers radiation 804. The radiation beam delivery system is shown only in a general fashion. It may be substantially similar to the radiation beam delivery system 40 shown in FIG. 5, or it may comprise additional or alternative components. In the present example, the radiation beam delivery system 802 has a fixed focal length 806, and delivers radiation that is focused at a focal point 808. The depth of focus of the radiation beam delivery system is illustrated by the ellipsoid 810. As is well known, an object located within the depth of focus of an optical system is considered to be in acceptable focus. The extent of the spatial region of acceptable focus in the Z-direction is highlighted by the horizontal lines 812. For purposes of the present example, any objects located within the region of acceptable focus could be utilized in a metrology measurement, and would yield results with an acceptable tolerance. The specific tolerances to be used for a particular product structure may, of course, be pre-defined, or may alternatively be defined by a user according to the user's requirements.

As discussed above, product structures may have a structure height that is taller than the depth of focus of the radiation beam delivery system. This is illustrated by exemplary product structure 814 positioned on a substrate 816. As can be seen, the top portion of the product structure is within the region of acceptable focus, but the bottom of the product structure is outside the region of acceptable focus. In other terms, a target structure located at the bottom portion of the product structure would not be sufficiently in focus to yield and acceptable result in a metrology measurement.

In FIG. 8(b), the radiation beam delivery system is translated in the Z-direction (illustrated by the arrow 818) from the initial position illustrated in FIG. 8(a). The focal point of the delivery system has been translated accordingly towards the surface of the substrate. As can be seen, a central portion of the product structure 814 is now within the region of acceptable focus (indicated by horizontal lines 820).

Figures 8C, 8D:
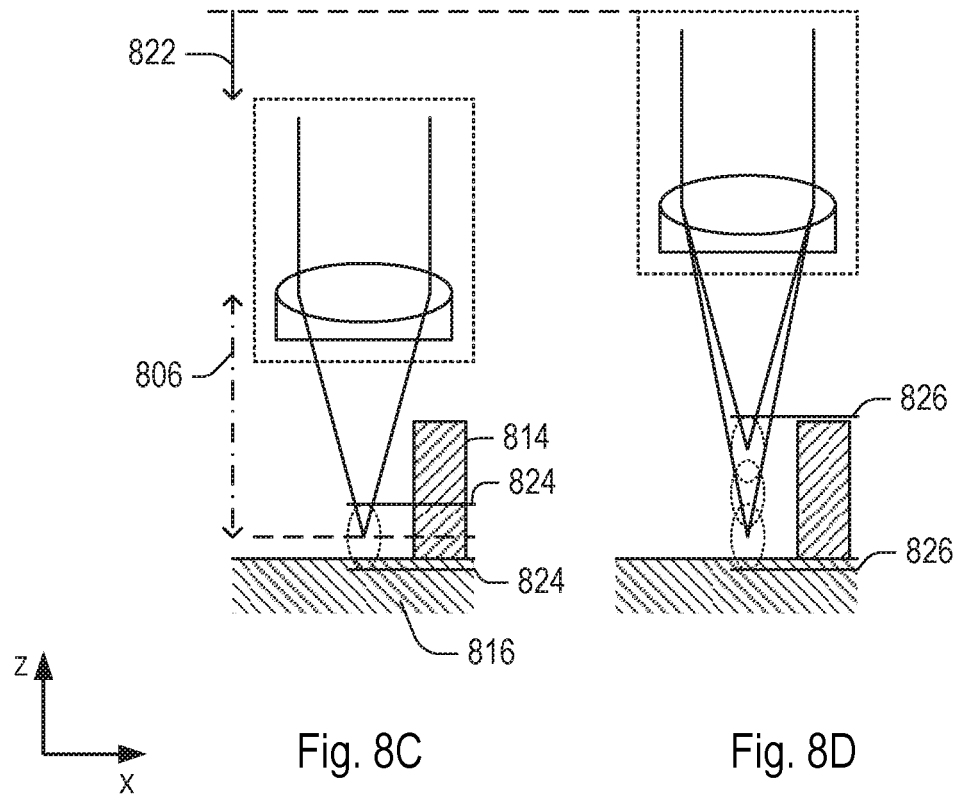

In FIG. 8(c), the radiation beam delivery system 802 is translated in the Z-direction (illustrated by arrow 822) further towards the substrate compared with the position illustrated in FIG. 8(b). In this situation, the bottom portion of the product structure 814 and the surface of the substrate 816 are within the region of acceptable focus (indicated by the horizontal lines 824).

In each of FIGS. 8(a)-8(c), only a portion of the product structure 814 is within the region of acceptable focus at any given time. As shown in FIG. 8(d), by suitably combining the measurement results, the effective region of acceptable focus (indicated by the horizontal lines 826) can be extended to cover the entirety of the product structure 814.

In the example of FIG. 8, the entirety of the radiation beam delivery system 802 is shown to be translated in the Z-direction. It will of course be appreciated that this is for illustrative purposes only. A portion, e.g. one or more specific optical components, of the delivery system may in reality be translated so as to change the position of the focal point. In one example, only a single component of the radiation beam delivery system is translated. Alternatively, the radiation beam delivery system may be stationary and the substrate may be translated relative to the delivery system. In one example, the substrate may be positioned on a substrate table, which is moved in the Z-direction. In other examples, both the radiation beam delivery system, or a portion thereof, and the substrate may move simultaneously.

FIG. 9 illustrates a second exemplary principle of a controlling step. For ease of comparison with FIG. 8, elements of FIG. 9 similar to corresponding elements of FIG. 8 are labelled with reference signs similar to those used in FIG. 8, but with prefix "9" instead of "8".

Figures 9A, 9B:
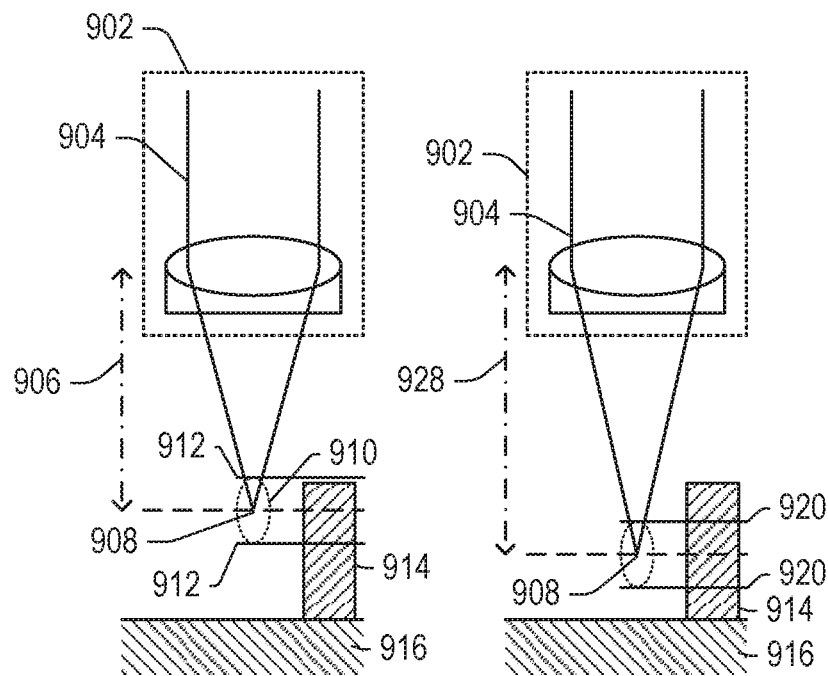
FIGS. 9A-9D illustrate a second principle of implementing a controlling step of the method of FIG. 7.

FIG. 9(a) is substantially identical to FIG. 8(a). A radiation beam delivery system 902 delivers radiation 904. The radiation beam delivery system has a focal length 906, and delivers radiation to a focal point 908. The depth of focus of the radiation beam delivery system is illustrated by the ellipsoid 910. As is well known, an object located within the depth of focus of an optical system is considered to be in acceptable focus. The spatial region of acceptable focus is highlighted by the horizontal lines 912.

In FIG. 9(b), the focal length 928 of the radiation beam delivery system is changed so as to shift the region of acceptable focus (indicated by the horizontal lines 920). Similarly to FIG. 8(b), the central portion of the product structure 914 is now located within the region of acceptable focus.

Figures 9C, 9D:
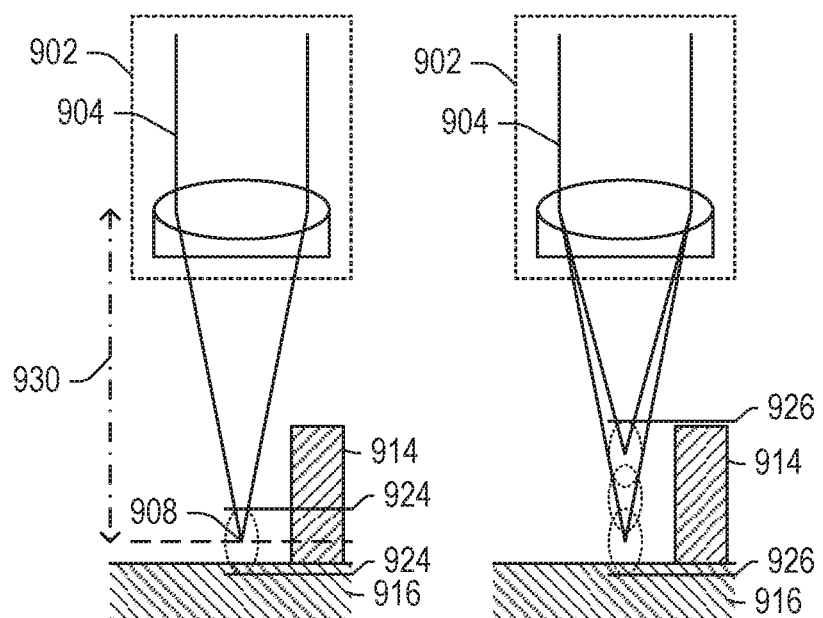

In FIG. 9(c), the focal length 930 is changed so as to shift the region of acceptable focus (indicated by horizontal lines 924). Similarly to FIG. 8(c), bottom portion of the product structure 914 and the surface of the substrate 916 are now within the region of acceptable focus.

In each of the three situations, only a portion of the product structure 914 is in focus at any given time. Similarly to FIG. 8(d), FIG. 9(d) illustrates how the measurement results of FIGS. 9(a)-9(c) may be by suitably combined, thereby extending the effective region of acceptable focus (indicated by the horizontal lines 926) to cover the entirety of the product structure 914.

It will be appreciated that changing the focal length may be accomplished in any suitable fashion. In one example, one or more of the optical components of the radiation beam delivery system may be translated relative to the delivery system. In another example, the focal length of one or more components may be changed directly (e.g. by using a lens with a variable focal length).

In the above examples, the position and/or focal length of the radiation beam delivery system, or individual components thereof, is changed. It should be noted, however, that examples wherein the position and/or focal length of the radiation collection system is changed may equally well be envisaged. Furthermore, examples may be envisaged wherein the position and/or focal length of both the radiation beam delivery system and the radiation collection system, or individual components thereof, may be changed.

It will be appreciated that the change in position of the focal point of the radiation beam delivery system and/or radiation collection system table may be implemented in a number of specific ways by the skilled person. In one example, the radiation beam delivery system comprises a controllable element (e.g. a lens component). Actuation of the lens component changes the position of the focal point of the radiation beam delivery system. The controllable element may in some examples form part of a focusing sub-system of the radiation beam delivery system. In one example, the controllable element is a lens component that comprises an actuator, the actuator being operable to actuate the lens component in a specific direction. The actuator is connected to a processor comprised in a control unit (e.g. the processing unit PU in FIG. 5).

In a known mode of operation, a focusing sub-system of the radiation beam delivery system receives an actuating signal from the processor. The actuating signal comprises focus setting information that is used, under typical operating conditions, to set a focus setting of the beam delivery system. It is to be noted that, in some examples, the focus setting is not changed during measurements. In other examples, however, the focus setting may be changed on a per-measurement basis.

In a specific example, the actuating signal additionally comprises actuating controlling information. The actuating controlling information is used to cause the controllable element to be actuated during the collection step. The actuating controlling information is not linked to the focus setting of the inspection apparatus. Rather, the actuating controlling information comprises movement data relating to an intended movement pattern for the controllable element during the collection step. In one example, the actuating controlling information is described by a simple function. In one specific example, the actuating controlling information is described by a so-called "sawtooth" function.

Two examples of a collection step will now be discussed with reference to FIG. 10.

Figure 10A:
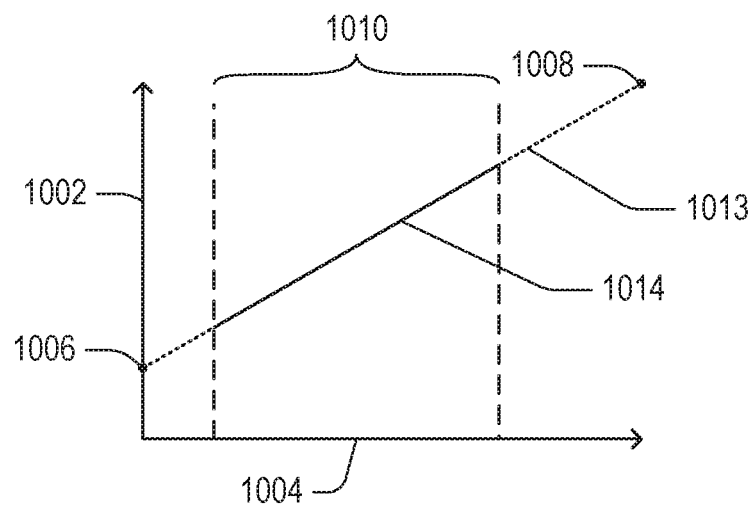
FIGS. 10A-10B are a schematic illustration of a collection step that may be implemented in the method of FIG. 7.
Figure 10B:
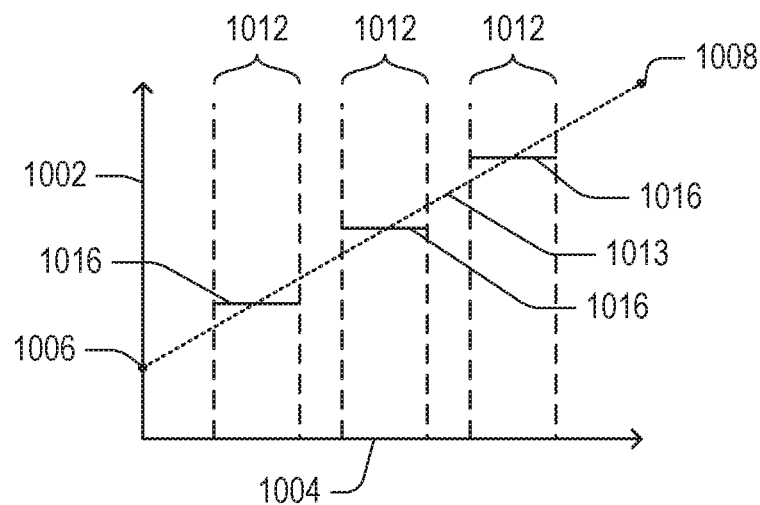

Both FIG. 10(a) and FIG. 10(b) show the position of the focal point 1002 (along the Y-direction) as a function of time 1004 (along the X-direction). In both examples, the position of the focal point is varied linearly between a first value 1006 and a second value 1008. This is indicated in FIG. 10 by line 1013. It will be appreciated that the linear variation between two values is exemplary only, and that any suitable type of variation and number of values may be used. In one example, the variation curve may be substantially sinusoidal.

FIG. 10(a) shows an example wherein the position of the focal point is changed during a single detection period 1010 (highlighted by line 1014). The change may be effected in any suitable fashion, as described above. During the detection period, the detector receives collected radiation from the target.

In FIG. 10(b), a plurality of detection periods 1012 are used. In the example shown in FIG. 10(b), during each detection period, the position of the focal point is kept constant (as indicated by lines 1016). However, as can be seen, when taken over all of the detection periods, the position of the focal point is changed linearly (as indicated by line 1013) in a manner similar to that shown in FIG. 10(*a*). In an alternative example, during each detection period, the position of the focal point is varied linearly, as described with reference to FIG. 10(*a*). In essence, each of the detection periods 1012 of FIG. 10(*b*) are analogous the detection period 1010 of FIG. 10(*a*).

Further embodiments according to the invention are presented in below numbered clauses:

1. A focus monitoring arrangement for an optical system, comprising:
    a focusing beam delivery system for delivering to said optical system focusing radiation, the optical system being arranged to deliver the focusing radiation to a target;
    a focusing beam collection system for collecting said focusing radiation after reflection from the target;
    a focus detection system comprising a detector for receiving the collected focusing radiation collected by the focusing beam collection system; and
    a focus control system for controlling a characteristic of at least one of the focusing radiation or the collected focusing radiation,
    wherein the focus detection system is operable to receive collected focusing radiation for a plurality of values of the characteristic.
2. A focus monitoring arrangement according to clause 1, wherein the detector receives collected focus radiation during a first period, and wherein the focus control system is operable to control the characteristic between at least two values during the first period.
3. A focus monitoring arrangement according to clause 1, wherein the detector receives collected focus radiation during a first plurality of periods, and wherein the focus control system is operable to control the characteristic so as to have a unique value for each period in the first plurality of periods.
4. A focus monitoring arrangement according to any previous clause, wherein the focus control system is operable to control the characteristic by controlling the position of an element of the optical system.
5. A focus monitoring arrangement according to clause 4, wherein the optical system comprises a substrate table for a substrate having a target, and wherein the focus control system is operable to control a position of the substrate table.
6. A focus monitoring arrangement according to clause 4 or 5, wherein the focusing beam delivery system comprises at least one optical component, and wherein the focus control system is operable to control a position of the at least one optical component.
7. A focus monitoring arrangement according to claim 4, 5 or 6, wherein the focusing beam collection system comprises at least one optical component, and wherein the focus control system is operable to control a position of the at least one optical component.
8. A focus monitoring arrangement according to any previous clause, wherein the focus detection system comprises a processing unit operable to process the collected focusing radiation received by the detector.
9. A method for a focus monitoring arrangement, comprising:
    delivering to an optical system focusing radiation, the optical system being arranged to deliver the focusing radiation to a target;
    collecting said focusing radiation after reflection from the target;
    receiving the collected focusing radiation at a detector; and
    controlling a characteristic of at least one of the focusing radiation or the collected focusing radiation, wherein
    receiving the collected focusing radiation comprises receiving focusing radiation for a plurality of values of the characteristic.
10. A method according to clause 9, wherein the step of receiving the collected focusing radiation is carried out during a first period, and wherein the step of controlling further comprises controlling the characteristic between at least two values during the first period.
11. A method according to clause 9, wherein the step of receiving the collected focusing radiation is carried out during a first plurality of periods, and wherein the step of controlling further comprises controlling the characteristic so as to have a unique value for each period in the first plurality of periods.
12. A method according to any of clauses 9 to 11, wherein the step of controlling the characteristic further comprises controlling the position of an element of the optical system.
13. A method according to clauses 12, wherein the optical system comprises a substrate table for a substrate having a target, and wherein the step of controlling comprises controlling a position of the substrate table.
14. A method according to clauses 12 or 13, wherein the optical system comprises a focusing beam delivery system having at least a first optical component, and wherein the step of controlling further comprises controlling a position of the first optical component.
15. A method according to any of clauses 12 to 14, wherein the optical system comprises a focusing beam collection system having at least a second optical component, and wherein the step of controlling further comprises controlling a position of the second optical component.
16. A method according to any of clauses 8 to 15, further comprising processing the collected focusing radiation received by the detector.
17. A computer program product comprising machine readable instructions which, when run on a suitable processor, cause the processor to control the focus control system to perform the controlling steps of any of claims 9 to 16.
18. A computer program product comprising machine readable instructions which, when run on a suitable processor, cause the processor to perform the processing step of claim 16.

Although specific reference may have been made above to the use of embodiments of the invention in the context of optical lithography, it will be appreciated that the invention may be used in other applications, for example imprint lithography, and where the context allows, is not limited to optical lithography. In imprint lithography, a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The descriptions above are intended to be illustrative, not limiting. Thus, it will be apparent to one skilled in the art that modifications may be made to the invention as described without departing from the scope of the claims set out below.

The invention claimed is:

1. A method for increasing a depth of focus of an optical system in an inspection apparatus, the method comprising:
    delivering radiation two or more times along a delivery path to a target using a radiation beam delivery system, wherein each radiation delivery focuses at a different position along the delivery path, and wherein the target has a dimension, as measured parallel to the delivery path, that exceeds a dimension of the depth of focus along the delivery path;
    collecting radiation scattered by the target after each radiation delivery using a radiation collection system;
    detecting the collected radiation using a detector;
    determining dark field detection results based on the collected radiation; and
    combining the dark field detection results to produce an extended depth of focus having a dimension that exceeds the dimension of the target.

2. The method of claim 1, wherein each radiation delivery occurs while varying a position of a focal point of the optical system during a period.

3. The method of claim 2, wherein the varying the position of the focal point of the optical system comprises a linear variation.

4. The method of claim 1, further comprising actuating at least one controllable element of the optical system.

5. The method of claim 4, wherein:
    the optical system comprises a substrate table configured to vary a position of the target so as to vary a position of a focal point of the optical system relative to the target along the delivery path; and
    the actuating comprises moving a position of the substrate table.

6. The method of claim 4, wherein:
    the radiation beam delivery system comprises an optical component; and
    the actuating comprises moving a position of the optical component so as to vary a position of a focal point of the optical system relative to the target along the delivery path.

7. The method of claim 4, wherein:
    the radiation collection system comprises an optical component; and
    the actuating comprises moving a position of the optical component so as to vary a position of a focal point of the optical system relative to the target along the delivery path.

8. The method of claim 4, wherein the actuating comprises transmitting an actuating signal to the at least one controllable element using a processor.

9. The method of claim 8, wherein the actuating signal comprises focus setting information and actuation controlling information.

10. The method of claim 1, further comprising processing the detected collected radiation using a processor to generate an actuating signal.

11. An inspection apparatus comprising:
    an optical system comprising:
        a radiation beam delivery system configured to deliver radiation two or more times along a delivery path to a target, wherein each radiation delivery focuses at a different position along the delivery path, and wherein the target has a dimension, as measured parallel to the delivery path, that exceeds a dimension of a depth of focus of the optical system along the delivery path;
        a radiation collection system configured to collect radiation scattered by the target after each radiation delivery; and
        a detection system configured to detect the collected radiation,
    wherein the optical system is configured to:
        determine dark field detection results based on the collected radiation, and
        combine the dark field detection results to produce an extended depth of focus having a dimension that exceeds the dimension of the target.

12. A lithographic apparatus comprising:
    an inspection apparatus comprising an optical system, the optical system comprising:
        a radiation beam delivery system configured to deliver radiation two or more times along a delivery path to a target, wherein each radiation delivery focuses at a different position along the delivery path, and wherein the target has a dimension, as measured parallel to the delivery path, that exceeds a dimension of a depth of focus of the inspection apparatus along the delivery path;
        a radiation collection system configured to collect radiation scattered by the target after each radiation delivery; and
        a detection system configured to detect the collected radiation,
    wherein the optical system is configured to:
        determine dark field detection results based on the collected radiation,
        combine the dark field detection results to produce an extended depth of focus having a dimension that exceeds the dimension of the target.

13. A computer program product comprising a computer readable medium having instructions stored thereon, that, when executed on a processor, cause the processor to control an optical system to perform operations, the operations comprising:
    delivering radiation two or more times along a delivery path to a target using a radiation beam delivery system, wherein each radiation delivery focuses at a different position along the delivery path; and wherein the target has a dimension, as measured parallel to the delivery path, that exceeds a dimension of a depth of focus of the optical system along the delivery path;

collecting radiation scattered by the target after each radiation delivery using a radiation collection system;

detecting the collected radiation using a detector;

determining dark field detection results based on the collected radiation; and combining the detection results to produce an extended depth of focus having a dimension that exceeds the dimension of the target.

14. A computer program product comprising a computer readable medium having instructions stored thereon, that, when executed on a processor, cause the processor to control an inspection apparatus to perform operations, the operations comprising:

delivering radiation two or more times along a delivery path to a target using a radiation beam delivery system, wherein each radiation delivery focuses at a different position along the delivery path, and wherein the target has a dimension, as measured parallel to the delivery path, that exceeds a dimension of a depth of focus of the inspection apparatus along the delivery path;

collecting radiation scattered by the target after each radiation delivery using a radiation collection system;

detecting the collected radiation using a detector;

determining dark field detection results based on the collected radiation;

processing the detected collected radiation to generate an actuating signal for controlling a controllable element in the inspection apparatus; and combining the dark field detection results to produce an extended depth of focus having a dimension that exceeds the dimension of the target.

15. The method of claim 2, wherein the varying the position of the focal point of the optical system comprises varying in a sinusoidal manner.

16. The method of claim 1, wherein the detecting comprises detecting at least a first diffraction order of the collected radiation.

17. The method of claim 1, further comprising excluding a zeroth diffraction order from the detected collected radiation to yield the dark field detection results.

18. The method of claim 17, wherein the excluding the zeroth diffraction order comprises blocking the zeroth diffraction order using an aperture structure upstream of the detector.

19. The method of claim 1, further comprising determining at least an overlay discrepancy between at least two layers generated by lithographic processes of the target.

20. The method of claim 1, further comprising generating a dark field image based on the combined dark field detection results, wherein the generated dark field image comprises at least two in-focus regions of the target, and wherein the at least two in-focus regions are separated by a distance, measured parallel to the delivery path, that exceeds the dimension of the depth of focus.

* * * * *